United States Patent [19]

Campana et al.

[11] Patent Number: 5,171,324
[45] Date of Patent: Dec. 15, 1992

[54] PROSTHETIC HIP STEM IMPLANT WITH TORQUE ADAPTER

[75] Inventors: Donna L. Campana, Warsaw; Perry A. Geremakis, South Bend; Mark D. Landes; Robert R. Kenyon, both of Warsaw, all of Ind.

[73] Assignee: Zimmer, Inc., Warsaw, Ind.

[21] Appl. No.: 899,056

[22] Filed: Jun. 16, 1992

Related U.S. Application Data

[63] Continuation of Ser. No. 827,525, Jan. 29, 1992, abandoned, which is a continuation of Ser. No. 609,338, Nov. 5, 1990, abandoned.

[51] Int. Cl.⁵ .......................... A61F 2/36; A61F 5/00
[52] U.S. Cl. ........................................ 623/23; 623/18; 606/86; 606/99
[58] Field of Search ................. 623/16, 18, 22, 23; 606/53, 60, 79, 80, 85-87, 89, 99, 100

[56] References Cited

U.S. PATENT DOCUMENTS

| | | | |
|---|---|---|---|
| 4,399,813 | 8/1983 | Barber | 606/99 |
| 4,642,121 | 2/1987 | Keller | 623/23 X |
| 4,728,334 | 3/1988 | Spotorno | 623/23 |
| 4,922,898 | 5/1990 | Dunn | 623/16 X |
| 4,936,863 | 6/1990 | Hofmann | 623/23 |
| 5,002,581 | 3/1991 | Paxson et al. | 623/18 X |

FOREIGN PATENT DOCUMENTS

| | | | |
|---|---|---|---|
| 0207873 | 1/1987 | European Pat. Off. | |
| 0243298 | 4/1987 | European Pat. Off. | |
| 0327509 | 2/1989 | European Pat. Off. | |
| 0339530 | 11/1989 | European Pat. Off. | 623/23 |
| 2101002 | 5/1972 | Fed. Rep. of Germany | |
| 2178320 | 7/1989 | United Kingdom | |

Primary Examiner—Ronald Frinks
Attorney, Agent, or Firm—Todd A. Dawson

[57] ABSTRACT

A prosthetic hip stem implant and torque wrench adapter. The hip stem includes an extraction bore formed through its body and a plurality of recessions formed in the body upper surface. A lip extends outwardly of the body and including alignment indicia for visually aligning the implant during seating. The torque wrench adapter includes a movable arm which is accommodated in the extraction bore of the implant. A pair of protrusions extending downwardly from the adaptor head to engage the implants' recesses. An adjustment screw shifts the arm toward the protrusions to clamp the adapter to the implant.

7 Claims, 2 Drawing Sheets

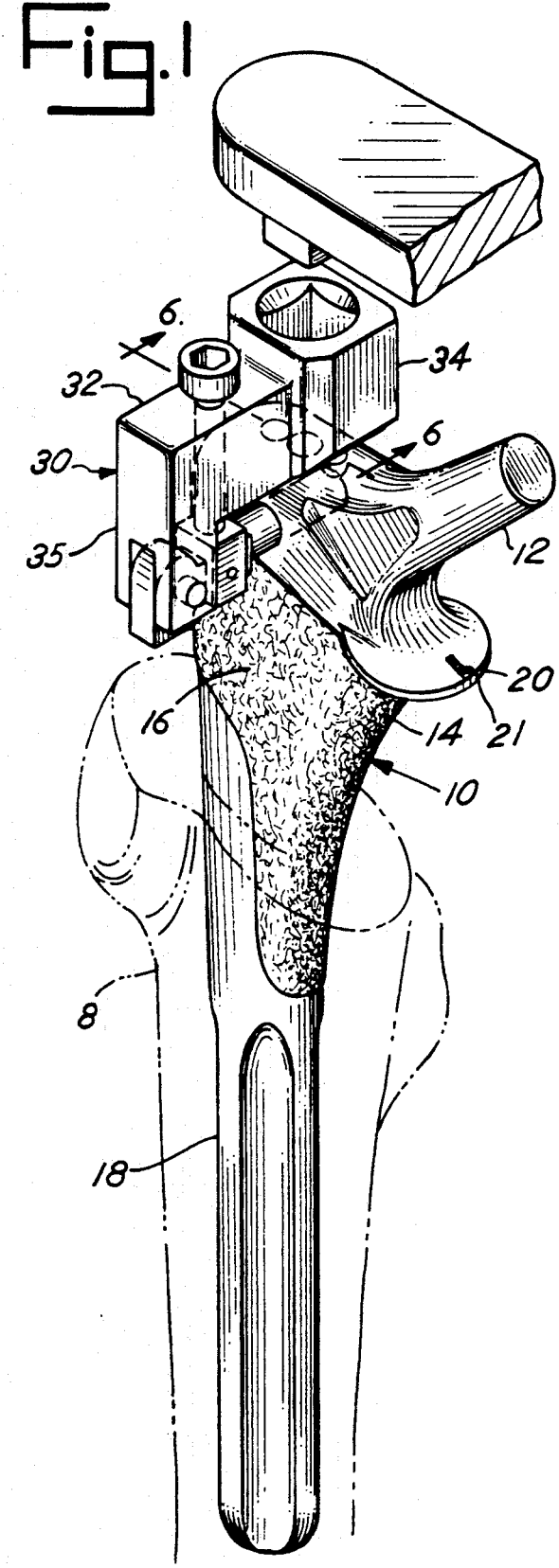
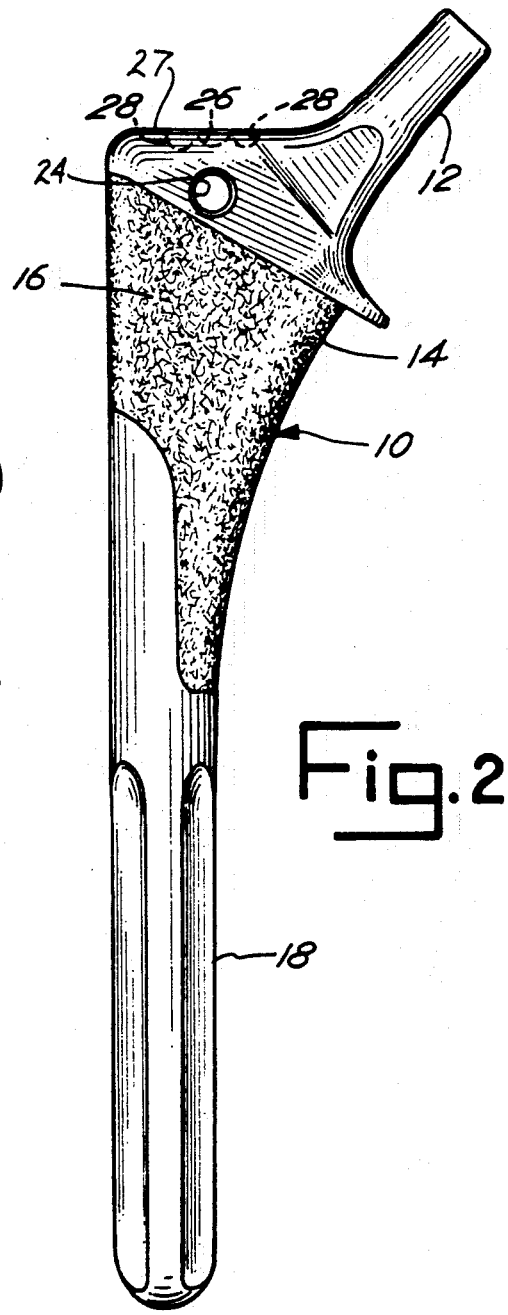
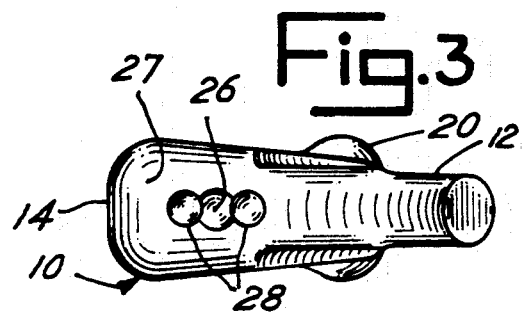

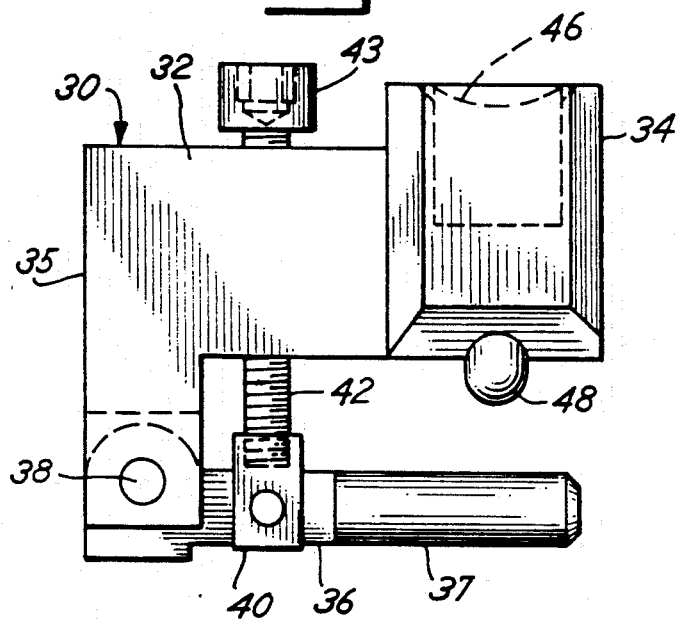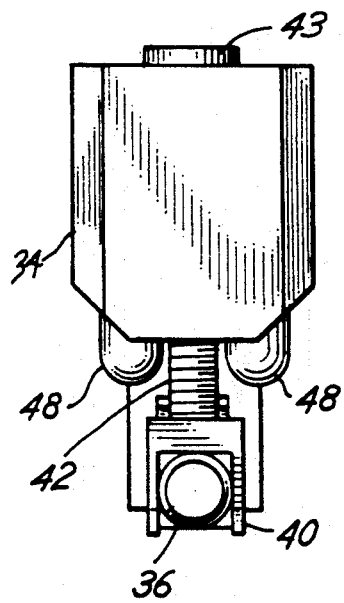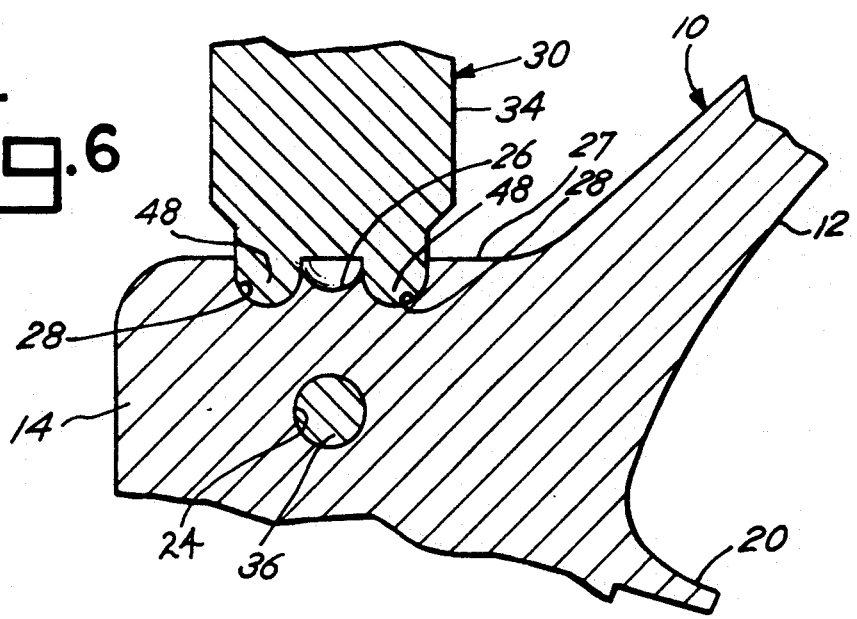

PROSTHETIC HIP STEM IMPLANT WITH TORQUE ADAPTER

This application is a continuation of application Ser. No. 07/827,525 filed Jan. 29, 1992, now abandoned, which in turn is a continuation of application Ser. No. 07/609,338 filed Nov. 5, 1990, now abandoned.

FIELD OF THE INVENTION

This invention relates generally to a prosthetic hip stem implant and more particularly to a prosthetic hip stem implant with a torque adapter.

BACKGROUND OF THE INVENTION

In hip replacement surgery where the head and neck of the posterior femur are removed and replaced with a prosthetic implant it is desirable that the implant be secured against rotational movement. A procedure and apparatus for torsionally testing a seated prosthetic hip implant has been developed to cure this problem and forms the subject matter of U.S. Pat. No. 4,922,898 issued to Dunn. As described in the Dunn Patent an adapter having parallel legs is fitted over the neck of a prosthetic hip implant after the implant has been seated. A torque wrench is connected to the adapter and torque applied to the implant. A properly seated implant will sustain 60 inch pounds of torque for a period of 15 seconds as described in Dunn. A problem exists, however, in that the neck of the implant may become scratched or otherwise marred when the adapter is attached. Scratches or imperfections in the surface of a prosthetic hip stem implant may create stress risers leading to a weakened implant.

Another problem with prior art hip stems is that during seating of the implant the surgeon is left to axially align the implant. The absence of alignment indicia could result in slight axial misalignment of the implant requiring its reseating.

SUMMARY OF THE INVENTION

The prosthetic hip stem and torque adapter of this invention eliminates the problems experienced above. The adapter includes a pivotal cylindrical arm engaging an extraction bore in the implant. The adapter further includes a pair of nipples which engage within a corresponding pair of recesses formed in the upper surface of the implant neck. The arm is drawn upwardly by an adjustment screw to clamp the adapter to the implant without allowing for the possibility of scratching the implant. The adapter further includes a head for connection to a torque wrench.

The implant of this invention includes alignment indicia on a protruding lip to provide alignment guidance for the surgeon when inserting the implant into the posterior femur.

Accordingly, it is an object of this invention to provide for a novel prosthetic hip stem implant.

Another object of this invention is to provide for a novel torque adapter for a prosthetic hip stem implant.

Another object of the invention is to provide for a torque adapter for a prosthetic hip stem implant which engages a through bore of the implant and recesses formed in the implant's upper surface to secure the adapter to the implant.

Other objects of the invention will become apparent upon a reading of the following description taken with the accompanying drawings.

BRIEF DESCRIPTION OF THE DRAWINGS

FIG. 1 is a perspective view of the prosthetic hip stem implant with torque adaptor attached. A portion of a prepared distal femur and torque wrench is shown in for illustrative purposes only.

FIG. 2 is a side elevational view of the prosthetic hip stem implant of this invention.

FIG. 8 is a top view of the prosthetic hip stem implant of FIG. 2.

FIG. 4 is a side elevational view of the torque adaptor of this invention.

FIG. 5 is a front view of the torque adaptor of FIG. 4.

FIG. 6 is a fragmented cross sectional view taken from line 6—6 of FIG. 1.

DESCRIPTION OF THE PREFERRED EMBODIMENT

The preferred embodiment herein described is not intended to be exhaustive or to limit the application to the precise forms disclosed. Rather it is chosen so that others skilled in the art may utilize its teachings.

Referring now to the drawings, a prosthetic hip stem implant 10 and torque adapter 30 are illustrated. Implant 10 includes a neck 12 and a fluted stem 18 joined by a body 14 at their junction. Neck 12 is adapted to accommodate a prosthetic hip ball (not shown). Stem 18 is adapted for insertion into the intramedullary canal of a femur 8 shown in broken lines in FIG. 1 only. A fiber metal porous surface layer 16 is carried by implant 10 on body 14 A lip or collar 20 extends from body 14 of implant 10 and includes alignment indicia 21 aligned with the longitudinal center line of the implant. An extraction bore 24 extends through body 14. A punch recess 26 having an arcuate bottom is formed in the upper surface 27 of body 14 and defines a striking point for impacting the implant into the femur intramedullary canal. A pair of recesses 28 are formed on the upper surface 27 of body 14 on opposite sides of punch recess 26.

Adapter 80 includes a generally L-shaped housing 82 having a head 34 as an integral part. Head 34 includes an interior squared socket 46 and a pair of lower extending nipples 48. An arm 36 is pivotally or movably connected to the lower extending leg 35 of housing 32 by a pivot pin 38. Arm 36 includes a cylindrical portion 37. A bracket 40 is connected to arm 36 between the leg of housing 32 and the cylindrical portion 37 of the arm. An adjustment screw 42 extends through body 32 and is threaded into bracket 40. Adjustment screw 42 includes a common hex head socket 43 which extends above body 32. In the alternative the adjustment screw 42 could move the arm 36 and cylindrical portion 37 up and down relative to a slot formed in the leg 35 for receiving the end of arm 36.

In use after the intramedullary canal of the femur is properly prepared the fluted stem 18 of the implant 10 is inserted into the canal. The surgeon drives the implant into seating engagement with the femur by placing one end of a punch (not shown) within central punch recess 26 and striking the opposite end of the punch. As the implant is driven into the canal the surgeon can insure axial alignment of the implant by aligning the alignment indicia 21 on lip 20 of the implant with a predetermined point on the femur. This point is referenced from a similar indicia on a rasp instrument which properly prepares the canal. To remove the implant from the intramedullary canal during the operation, the surgeon inserts a removal tool (not shown) through extraction bore 24 of the implant and pulls the implant out.

After implant 10 is seated within the femur intramedullary canal, the implant must be tested against rotation under torque to insure proper fit of the implant to the femur. To attach a torque wrench the surgeon attaches adapter 30 to the implant by inserting arm 36 into extraction bore 24. Properly positioned, nipples 48 of adapter head 34 seat within recesses 28 of the implant. Screw 42 is then turned to pivot arm 36 toward head 34 to clamp the adapter to the implant 10. After the adapter is firmly attached to the implant the square drive of a torque wrench partially shown in FIG. 1 only is fit within socket 46 of adapter head 34. To remove the adapter, adjustment screw 42 is rotated in an opposite direction to pivot arm 36 away from head 34 to relieve the clamping pressure of the arm. The adapter may be then slid from implant 10.

As illustrated and described adapter 30 when connected to implant 10 the adaptor only contacts the implant at the inner surface of extraction bore 24 and at recesses 28. Further, the implant is only contacted by rounded surfaces of the adapter. Therefore, the possibility of damaging or scratching the implant with the adapter during use is minimized.

It should be understood that the invention should not be limited to the precise forms disclosed but may be modified within the scope of the approved claims.

We claim:

1. A prosthetic hip implant including a stem and a neck, said stem including an upper surface near said neck, said upper surface extending away from said neck such that said surface is generally rectangular, means formed in said stem upper surface for engagement by a torque wrench adapter and a punch recess formed in the upper surface for engagement with a driver instrument, said means including a pair of recesses formed in the upper surface on opposite sides of the punch recess such that the pair of recesses, the punch recess and the neck are in linear alignment along the upper surface of the stem.

2. In combination a prosthetic hip implant and a torque wrench adapter, said implant including a stem and a neck forming a body at their junction, said body having an upper surface, an extraction bore formed through said body below said upper surface, engagement means formed in said body upper surface for engagement by said adapter, said adapter including a body, an arm connected to said body for insertion within said extraction bore, said body including a socket for accommodating a torque wrench drive, a protrusion means extending toward said arm for seating within said engagement means, a portion of said body being disposed between said arm and said protrusion means, and means for clamping said adapter to said implant.

3. The combination of claim 2 wherein said engagement means includes at least one recess, said clamping means includes a screw connected to said arm by a bracket wherein rotation of said screw in one direction causes said arm to shift toward said body for clamping engagement of said body between said arm and said protrusion means.

4. A torque wrench adapter for a prosthetic hip implant, said implant having an extraction bore and upper engagement means, said adapter comprising a housing, an arm movably connected to said housing, said housing including a head, said head including socket means for accommodating a drive of a torque wrench, protrusion means carried by said housing for engaging said implant engagement means, said protrusion means being spaced from said arm, and means carried by said housing for shifting said arm toward said protrusion means.

5. The adapter of claim 4 wherein said shifting means includes a bracket connected to said arm adjacent said housing, a screw having a head and a shaft, said screw shaft traversing said housing and threaded within said bracket, said head extending outwardly of said housing, rotation of said screw draws said bracket towards said head to move a distal end of said arm toward said head.

6. A prosthetic hip implant including a lower depending stem and an upper neck held in angled relationship by a body, a lip extends outwardly from said body, and indicia on an upper surface of said lip in view of a surgeon as said implant is being positioned within a femur constituting means for providing visual alignment with said femur to a surgeon as said implant is seated within a femoral intramedullary canal.

7. The prosthetic hip implant of claim 6 in which said indicia is disposed on a top surface of said lip.

* * * * *